United States Patent [19]

Klaus et al.

[11] Patent Number: 5,700,836
[45] Date of Patent: Dec. 23, 1997

[54] AROMATIC CARBOXYLIC ACID DERIVATIVES

[75] Inventors: Michael Klaus, Weil am Rhein, Germany; Peter Mohr, Basel, Switzerland

[73] Assignee: Hoffmann-La Roche Inc., Nutley, N.J.

[21] Appl. No.: 734,222

[22] Filed: Oct. 21, 1996

Related U.S. Application Data

[62] Division of Ser. No. 294,466, Aug. 23, 1994, abandoned.

[30] Foreign Application Priority Data

Sep. 2, 1993 [CH] Switzerland .................. 2618/93
Jun. 21, 1994 [CH] Switzerland .................. 1960/94

[51] Int. Cl.$^6$ .................. A01N 37/10; A01N 37/18
[52] U.S. Cl. .................. 514/544; 514/617
[58] Field of Search .................. 514/544, 617

[56] References Cited

U.S. PATENT DOCUMENTS

| | | |
|---|---|---|
| 4,193,931 | 3/1980 | Loeliger . |
| 4,326,055 | 4/1982 | Loeliger . |
| 4,578,498 | 3/1986 | Frickel et al. . |
| 4,783,549 | 11/1988 | Lang et al. . |
| 4,801,733 | 1/1989 | Wuest et al. . |
| 4,889,847 | 12/1989 | Kligman et al. . |
| 4,992,574 | 2/1991 | Klaus et al. . |
| 5,019,569 | 5/1991 | Kligman et al. . |

FOREIGN PATENT DOCUMENTS

| | | |
|---|---|---|
| 0 002742 | 7/1979 | European Pat. Off. . |
| 0 169571 | 1/1986 | European Pat. Off. . |
| 0 315071 | 5/1989 | European Pat. Off. . |

OTHER PUBLICATIONS

Kagechika et al., J. of Med. Chem., vol. 32, No. 5, pp. 1098–1108 (1969).
Kagechika et al., Chem. Pharm. Bull., vol. 33, No. 12, pp. 5597–5600 (1985).
CA 111:23742 (1989).
CA 104:141730 (1985).

*Primary Examiner*—Paul J. Killos
*Attorney, Agent, or Firm*—Dennis P. Tramaloni; Alan P. Kass; Bruce A. Pokras

[57] ABSTRACT

Compounds of the formula

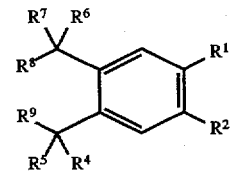

wherein $R^1$ is a residue of the formula

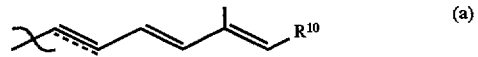

or

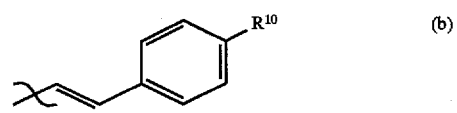

and $R^2$–$R^{10}$ have the significance given in the specification can be used as pharmaceuticals, particularly for the repair of photodamaged skin, other dermatological conditions, and oncological indications.

14 Claims, No Drawings

AROMATIC CARBOXYLIC ACID DERIVATIVES

This is a division of application Ser. No. 08/294,466, filed Aug. 23, 1994 abandoned.

SUMMARY OF THE INVENTION

The present invention is concerned with novel aromatic carboxylic acid derivatives of the formula:

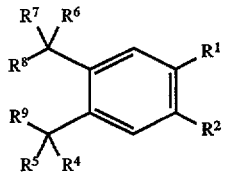

wherein $R^1$ is a group of the formula

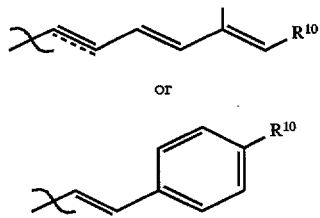

$R^2$ is $C_{2-8}$-alkanoyl, $C_{2-8}$-alkyl, $C_{2-8}$-alkenyl, $C_{2-8}$-alkynyl or —$OCH_2R^3$;

$R^3$ is hydrogen, $C_{1-6}$-alkyl, $C_{2-6}$-alkenyl or $C_{2-6}$-alkynyl;

$R^4$ to $R^9$ each independently are hydrogen or $C_{1-5}$-alkyl; or $R^8$ and $R^9$ together are $(CR^aR^b)_n$, $R^a$ and $R^b$ are hydrogen or $C_{1-5}$-alkyl, n is 1, 2 or 3 and $R^4$ to $R^7$ are the same as above; or $R^8$ and $R^9$ together are $(CR^aR^b)_n$ and $R^4$ and $R^6$ together are methylene or ethylene which are unsubstituted or substituted by hydroxy, and $R^a,R^b$, $R^5$, $R^7$ and n are the same as above;

$R^{10}$ is carboxyl, $C_{1-6}$-alkoxycarbonyl or mono- or di-$(C_{1-6}$-alkyl)carbamoyl and the dotted bond in formula (a) is optional;

and pharmaceutically acceptable salts of carboxylic acids of formula I.

DETAILED DESCRIPTION OF THE INVENTION

The present invention is concerned with novel aromatic carboxylic acid derivatives which are useful for treating photodamaged skin. The invention comprises compounds of the formula:

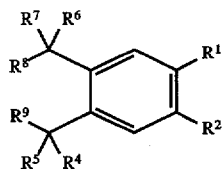

wherein $R^1$ is a group of the formula:

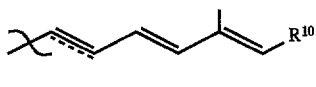

or

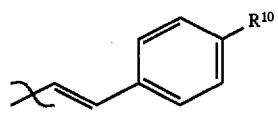

$R^2$ is $C_{2-8}$-alkanoyl, $C_{2-8}$-alkyl, $C_{2-8}$-alkenyl, $C_{2-8}$-alkynyl or —$OCH_2R^3$;

$R^3$ is hydrogen, $C_{1-6}$-alkyl, $C_{2-6}$-alkenyl or $C_{2-6}$-alkynyl;

$R^4$ to $R^9$ each independently are hydrogen or $C_{1-5}$-alkyl; or $R^8$ and $R^9$ together are $(CR^aR^b)_n$, $R^a$ and $R^b$ are hydrogen or $C_{1-5}$-alkyl, n is 1, 2 or 3 and $R^4$ to $R^7$ are the same as above; or $R^8$ and $R^9$ together are $(CR^aR^b)_n$ and $R^4$ and $R^6$ together are methylene or ethylene, which can be substituted by hydroxy, and $R^a,R^b$, $R^5$, $R^7$ and n are the same as above;

$R^{10}$ is carboxyl, $C_{1-6}$-alkoxycarbonyl or mono- or di-$(C_{1-6}$-alkyl)carbamoyl and the dotted bond in formula (a) is optional;

and pharmaceutically acceptable salts of carboxylic acids of formula I.

Particularly, the invention comprises compounds of the formula:

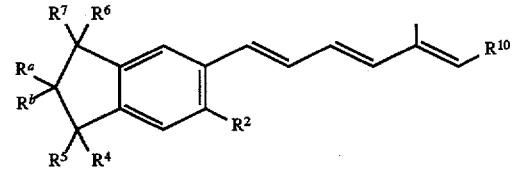

wherein $R^2$ is $C_{2-8}$-alkanoyl, $C_{2-8}$-alkyl, $C_{2-8}$-alkenyl, $C_{2-8}$-alkynyl or —$OCH_2R^3$;

$R^3$ is hydrogen, $C_{1-6}$-alkyl, $C_{2-6}$-alkenyl or $C_{2-6}$-alkynyl;

$R^5$ and $R^7$ each independently are hydrogen or $C_{1-5}$-alkyl;

$R^4$ and $R^6$ each independently are hydrogen or $C_{1-5}$-alkyl, or taken together are methylene or ethylene which are unsubstituted or substituted by hydroxy;

$R^a$ and $R^b$ each are independently hydrogen or $C_{1-5}$-alkyl;

$R^{10}$ is carboxyl, $C_{1-6}$-alkoxycarbonyl or mono- or di-$(C_{1-6}$-alkyl)carbamoyl;

and pharmaceutically acceptable salts of carboxylic acids of formula Ib. $R^a$ and $R^b$ are preferably hydrogen.

The invention also comprises compounds of the formula:

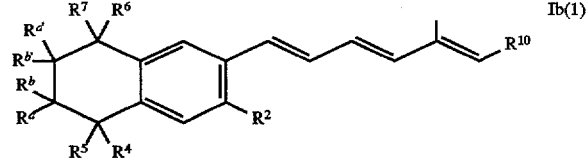

wherein $R^2$ is $C_{2-8}$-alkanoyl, $C_{2-8}$-alkyl, $C_{2-8}$-alkenyl, $C_{2-8}$-alkynyl or —$OCH_2R^3$;

$R^3$ is hydrogen, $C_{1-6}$-alkyl, $C_{2-6}$-alkenyl or $C_{2-6}$-alkynyl;

$R^5$ and $R^7$ each independently are hydrogen or $C_{1-5}$-alkyl;

$R^4$ and $R^6$ each independently are hydrogen or $C_{1-5}$-alkyl, or taken together are methylene or ethylene which are unsubstituted or substituted by hydroxy;

$R^a$, $R^{a'}$, $R^b$ and $R^{b'}$ each are independently hydrogen or $C_{1-5}$-alkyl;

$R^{10}$ is carboxyl, $C_{1-6}$-alkoxycarbonyl or mono- or di-($C_{1-6}$-alkyl)carbamoyl;

and pharmaceutically acceptable salts of carboxylic acids of formula Ib. $R^a$, $R^{a'}$, $R^b$ and $R^{b'}$ are preferably hydrogen.

The invention also comprises compounds of the formula:

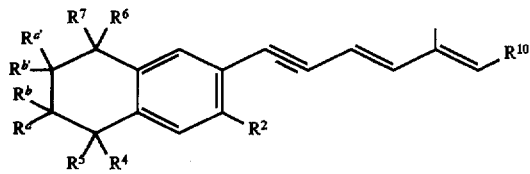

Ib(2)

wherein $R^2$ is $C_{2-8}$-alkanoyl, $C_{2-8}$-alkyl, $C_{2-8}$-alkenyl, $C_{2-8}$-alkynyl or $-OCH_2R^3$;

$R^3$ is hydrogen, $C_{1-6}$-alkyl, $C_{2-6}$-alkenyl or $C_{2-6}$-alkynyl;

$R^5$ and $R^7$ each independently are hydrogen or $C_{1-5}$-alkyl;

$R^4$ and R6 each independently are hydrogen or $C_{1-5}$-alkyl, or taken together are methylene or ethylene which are unsubstituted or substituted by hydroxy;

$R^a$, $R^{a'}$, $R^b$ and $R^{b'}$ each are independently hydrogen or $C_{1-5}$-alkyl;

$R^{10}$ is carboxyl, $C_{1-6}$-alkoxycarbonyl or mono- or di-($C_{1-6}$-alkyl)carbamoyl;

and pharmaceutically acceptable salts of carboxylic acids of formula Ib. $R^a$, $R^{a'}$, $R^b$ and $R^{b'}$ are preferably hydrogen.

The invention also comprises compounds of the formula:

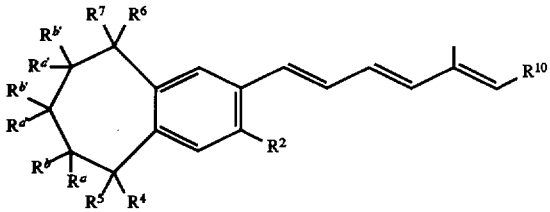

Ic wherein $R^2$ is $C_{2-8}$-alkanoyl, $C_{2-8}$-alkyl, $C_{2-8}$-alkenyl, $C_{2-8}$-alkynyl or $-OCH_2R^3$;

$R^3$ is hydrogen, $C_{1-6}$-alkyl, $C_{2-6}$-alkenyl or $C_{2-6}$-alkynyl;

$R^5$ and $R^7$ each independently are hydrogen or $C_{1-5}$-alkyl;

$R^4$ and R6 each independently are hydrogen or $C_{1-5}$-alkyl, or taken together are methylene or ethylene which are unsubstituted or substituted by hydroxy;

$R^a$, $R^{a'}$, $R^{1''}$, $R^b$ $R^{b'}$ and $R^{b''}$ each are independently hydrogen or $C_{1-5}$-alkyl;

$R^{10}$ is carboxyl, $C_{1-6}$-alkoxycarbonyl or mono- or di-($C_{1-6}$-alkyl)carbamoyl;

and pharmaceutically acceptable salts of carboxylic acids of formula Ic. $R^a$, $R^{a''}$, $R^b$ and $R^{b''}$ are preferably hydrogen. $R^{a'}$ and $R^{b'}$ are preferably hydrogen or methyl.

The invention also comprises compounds of the formula:

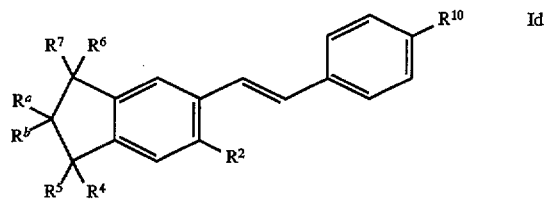

Id wherein $R^2$ is $C_{2-8}$-alkanoyl, $C_{2-8}$-alkyl, $C_{2-8}$-alkenyl, $C_{2-8}$-alkynyl or $-OCH_2R^3$;

$R^3$ is hydrogen, $C_{1-6}$-alkyl, $C_{2-6}$-alkenyl or $C_{2-6}$-alkynyl;

$R^5$ and $R^7$ each independently are hydrogen or $C_{1-5}$-alkyl;

$R^4$ and $R^6$ each independently are hydrogen or $C_{1-5}$-alkyl, or taken together are methylene or ethylene, which are unsubstituted or substituted by hydroxy;

$R^a$ and $R^b$ each are independently hydrogen or $C_{1-5}$-alkyl;

$R^{10}$ is carboxyl, $C_{1-6}$-alkoxycarbonyl or mono- or di-($C_{1-6}$-alkyl)carbamoyl;

and pharmaceutically acceptable salts of carboxylic acids of formula Id. $R^a$ and $R^b$ are preferably hydrogen.

The invention also comprises compounds of the formula:

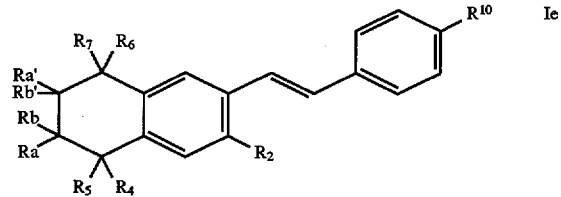

Ie wherein $R^2$ is $C_{2-8}$-alkanoyl, $C_{2-8}$-alkyl, $C_{2-8}$-alkenyl, $C_{2-8}$-alkynyl or $-OCH_2R^3$;

$R^3$ is hydrogen, $C_{1-6}$-alkyl, $C_{2-6}$-alkenyl or $C_{2-6}$-alkynyl;

$R^5$ and $R^7$ each independently are hydrogen or $C_{1-5}$-alkyl;

$R^4$ and $R^6$ each independently are hydrogen or $C_{1-5}$-alkyl, or taken together are methylene or ethylene which are unsubstituted or substituted by hydroxy;

$R^a$, $R^{a'}$, $R^b$ and $R^{b'}$ each are independently hydrogen or $C_{1-5}$-alkyl;

$R^{10}$ is carboxyl, $C_{1-6}$-alkoxycarbonyl or mono- or di-($C_{1-6}$-alkyl)carbamoyl;

and pharmaceutically acceptable salts of carboxylic acids of formula Ie. $R^a$, $R^{a'}$, $R^b$ and $R^{b'}$ are preferably hydrogen.

The invention also comprises compounds of the formula:

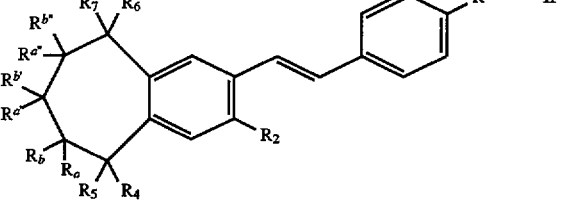

If wherein $R^2$ is $C_{2-8}$-alkanoyl, $C_{2-8}$-alkyl, $C_{2-8}$-alkenyl, $C_{2-8}$-alkynyl or $-OCH_2R^3$;

$R^3$ is hydrogen, $C_{1-6}$-alkyl, $C_{2-6}$-alkenyl or $C_{2-6}$-alkynyl;

$R^5$ and $R^7$ each independently are hydrogen or $C_{1-5}$-alkyl;

$R^4$ and $R^6$ each independently are hydrogen or $C_{1-5}$-alkyl, or taken together are methylene or ethylene which are unsubstituted or substituted by hydroxy;

$R^a$, $R^{a'}$, $R^{a''}$, $R^b$ $R^{b'}$ and $R^{b''}$ each are independently hydrogen or $C_{1-5}$-alkyl;

$R^{10}$ is carboxyl, $C_{1-6}$-alkoxycarbonyl or mono- or di-($C_{1-6}$-alkyl)carbamoyl;

and pharmaceutically acceptable salts of carboxylic acids of formula If. $R^a$, $R^{a''}$, $R^b$ and $R^{b''}$ are preferably hydrogen. $R^{a'}$ and $R^{b'}$ are preferably hydrogen or methyl.

In all the above embodiments of the invention, preferably $R^4$, $R^5$, $R^6$, and $R^7$ are independently, hydrogen or methyl, or $R^5$ and $R^7$ are independently hydrogen or methyl and $R^4$ and $R^6$ taken together are methylene or ethylene which are unsubstituted or substituted by hydroxy. In all the above embodiments of the invention, $R^{10}$ is preferably carboxyl, and $R^2$ is is preferably n-$C_{2-8}$ alkyl or —$OCH_2R^3$ wherein $R^3$ is hydrogen or n-$C_{1-6}$ alkyl.

The invention is furthermore concerned with pharmaceutical preparations comprising compounds of the invention or their salts and with a process for the manufacture of said compounds.

The terms "$C_{1-6}$", "$C_{2-6}$", "$C_{1-5}$", "$C_{1-7}$" and "$C_{2-8}$" used herein denote groups with 1–6, 2–6, 1–5, 1–7 and 2–8 carbon atoms. Alkyl residues $R^2$ and $R^3$ are preferably straight-chain alkyl residues such as ethyl, propyl, butyl, pentyl, hexyl, heptyl and octyl. Alkenyl residues $R^2$ and $R^3$ are preferably straight-chain alkenyl residues such as vinyl, 1- and 2-propenyl, and 2-butenyl. Alkynyl residues $R^2$ and $R^3$ are preferably ethynyl, 1- and 2-propynyl, 1- and 2-butynyl. $C_{2-8}$-alkanoyl residues are preferably straight-chain alkanoyl residues such as acetyl, propionyl, butyryl, pentanoyl, hexanoyl, heptanoyl and octanoyl.

The compounds of the invention and their salts can be manufactured in accordance with the invention by a) reacting a compound of the formula:

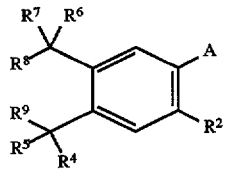

II with a compound of the formula:

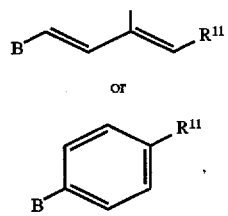

III or

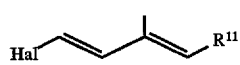

IV wherein one of the groups A and B is —$CH_2P(O)(OAlk)_2$ or —$CH_2P^+(Ph)_3Y^-$ and the other symbol A or B is formyl; Ph is phenyl or substituted phenyl; Alk is $C_{1-6}$-alkyl; and $Y^-$ is an anion and $R^{11}$ is $C_{1-6}$-alkoxy-carbonyl; and the remaining symbols have the significance given above;

or b) reacting a compound of the formula:

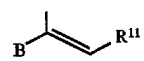

V with a compound of the formula:

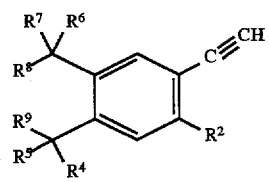

VI wherein Hal is bromine or iodine and $R^{11}$ is $C_{1-6}$-alkoxycarbonyl; and the remaining R-groups have the significance given above;

or c) reacting a compound of the formula:

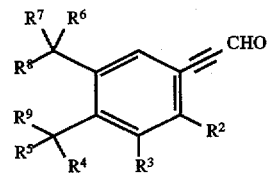

VII with a compound of the formula:

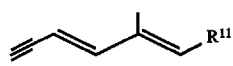

VIII wherein B is —$CH_2P(O)(OAlk)_2$ or —$CH_2P^+(Ph)_3Y^-$ and $R^{11}$ is $C_{1-6}$-alkoxycarbonyl, or d) reacting a compound of the formula:

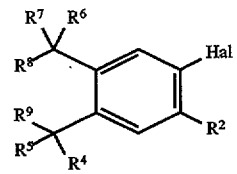

IX with a compound of the formula:

X wherein Hal is bromine or iodine and the remaining R-groups have the significance given above, or e) oxidizing the hydroxy group in a compound of the formula:

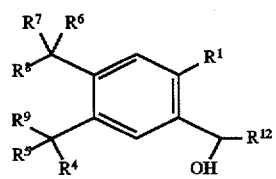

XI wherein $R^{12}$ is $C_{1-7}$-alkyl, to the oxo group, and, if desired, in the resulting compound of formula I converting the alkoxycarbonyl group, into a carboxyl group or a pharmaceutically acceptable salt thereof or into a mono- or di-$C_{1-6}$-(alkyl)carbamoyl group.

The foregoing reactions can be carried out according to methods known per se.

The reaction of the compounds II and III in accordance with process variant a) as well as VII and VIII in accordance with process variant c) can be carried out according to the known methods of the Wittig or Homer reaction.

In the case of the Wittig reaction, i.e., when using compounds of formulae II and III with A or B=—CH$_2$P$^+$(Ph)$_3$Y$^-$, the components are reacted with one another in the presence of an acid-binding agent, e.g. in the presence of a strong base, such as e.g. butyllithium, sodium hydride or the sodium salt of dimethyl sulphoxide, or K tert.butylate, but primarily in the presence of an ethylene oxide which is optionally substituted by lower alkyl such as 1,2-butylene oxide, optionally in a solvent, e.g. in an ether, such as diethyl ether or tetrahydrofuran, or in an aromatic hydrocarbon, such as benzene, in a temperature range lying between about –20° C. and the boiling point of the reaction mixture.

Of the inorganic acid anions Y$^-$ the chloride and bromide ion or the hydrosulphate ion is preferred and of the organic acid anions the tosyloxy ion is preferred. The residue Ph is preferably phenyl.

In the case of the Horner reaction, i.e., when using compounds of formulae II or III with A or B=—CH$_2$P(O)(OAlk)$_2$, the components are condensed with the aid of a base and preferably in the presence of an inert organic solvent, e.g., with the aid of sodium hydride in benzene, toluene, dimethylformamide, tetrahydrofuran, dioxan or 1,2-dimethoxy ethers or also with the aid of a sodium alcoholate in an alkanol, e.g., sodium methylate in methanol, in a temperature lying between about –20° C. and the boiling point of the reaction mixture.

The coupling reactions b) and d) can be catalyzed, starting directly from the acetylenes VI and, respectively, X, by phosphine complexes of palladium and nickel and Cu(I) salts. In all cases the presence of a base is convenient, for example an organic nitrogen base, such as triethylamine, piperidine or pyridine, or an alkali metal alcoholate, such as sodium methanolate or sodium phenolate. If desired, the reaction is carried out in a solvent, preferably in benzene, dimethylformamide or tetrahydrofuran. The reaction conveniently takes place at a temperature of 20° to 150° C.

The oxidation e) can be carried out with oxidation agents such as MnO$_2$ in an inert organic solvent e.g., a chlorinated hydrocarbon such as methylene chloride, preferably at room temperature.

Compounds of the invention in which R$^1$ represents a group of formula (a) in which the dotted bond is absent; or a group of formula (b); and R$^2$ is a group as defined above except an alkanoyl residue can be obtained according to process variant a).

Compounds of the invention in which R$^1$ represents a group (a) in which the dotted bond is present can be obtained according to process variants b), c) and d).

Compounds in which R$^2$ represents a C$_{2-8}$-alkanoyl residue are obtained according to process variant e).

The carboxylic acid ester group in a compound of the invention can be saponified to the carboxyl group and this can then be converted into a salt or an amide.

A carboxylic acid ester of the invention can be amidated directly as described hereinafter or can be hydrolyzed in a manner known per se, e.g., by treatment with alkali, especially by treatment with aqueous-alcoholic sodium or potassium hydroxide, in a temperature range lying between room temperature and the boiling point of the reaction mixture, to the carboxylic acid which can be amidated via an acid halide.

A carboxylic acid of the invention can be converted in a manner known per se, e.g., by treatment with thionyl chloride, or phosphorus trichloride in toluene or oxalyl chloride in DMF/benzene into the acid chloride which can be converted by reaction with alcohols into esters or with amines into the corresponding amide.

A carboxylic acid ester of the invention can be converted directly into the corresponding amide, e.g. by treatment with lithium amide. The lithium amide is advantageously reacted with the particular ester at room temperature.

All of these conversions can be carried out according to methods known per se.

Examples of pharmaceutically acceptable salts into which the carboxylic acids of the invention can be converted are alkali metal salts, such as Na and K salts, alkaline earth metal salts, such as Ca and Mg salts, and ammonium salts, e.g. salts with alkylamines and hydroxyalkylamines or with other organic bases, such as dimethylamine, diethanolamine and piperidine.

The compounds of the invention can occur as E/Z isomer mixtures which can be separated according to methods known per se. The E-(all-E) isomers are preferred.

The compounds of formulae II-X, insofar as they are not known or their preparation is not described hereinafter, can be prepared in analogy to known procedures or procedures described hereinafter.

The compounds in accordance with the invention act as selective ligands of retinoic acid γ-receptors (RAR-γ). They can be used for the treatment of photodamaged skin. The compounds of the invention are also useful for the prophylaxis of photo- and age-damaged skin and for treating age-damaged skin as well as for the promotion of wound healing, for example of incised wounds, such as surgical wounds, wounds caused by burns and other wounds caused by cutaneous trauma. The utility of the compounds in accordance with the invention for this purpose can be determined by any conventional means. Preferably, the determination is made using the models described in *Science*, 237:1333–1336 (1987) and *J. Pathol.*, 1;29:601–613 (1987). The utility of the compounds of the invention to repair photo-damaged skin is preferably determined through the hairless mouse procedure described below.

Furthermore, the compounds in accordance with the invention can be used for the therapy and prophylaxis of dermatological disorders which are accompanied by epithelial lesions, e.g., acne and psoriasis, as well as malignant and premalignant epithelial lesions, tumours and precancerous changes to the mucous membrane in the mouth, tongue, larynx, oesophagus, bladder, cervix and colon.

The compounds of the invention and their salts can accordingly be used in the form of pharmaceutical preparations.

The preparations for systemic use can be produced, e.g., by adding a compound of the invention or a salt thereof as the active ingredient to non-toxic inert solid or liquid carriers which are usual in such preparations.

The preparations can be administered enterally, parenterally or topically. Preparations in the form of tablets, capsules, dragees, syrups, suspensions, solutions and suppositories are, e.g., suitable for enteral administration. Preparations in the form of infusion or injections solutions are suitable for parental administration.

For enteral and parental administration the compounds of formula I can be administered to adults in amounts of about 1–100mg, preferably 5–30 mg/day.

For topical use the active ingredients are conveniently used in the form of ointments, tinctures, creams, solutions, lotions, sprays, suspensions and the like. Ointments and creams as well as solutions are preferred. These preparations designed for topical use can produced by mixing the active ingredients with non-toxic, inert solid or liquid carriers which are suitable for topical treatment and which are usual in such preparations.

For topical use there are conveniently suitable about 0.1–5%, preferably 0.3–2%, solutions as well as about 0.1–5%, preferably 0.3–2%, salves or creams;

If desired, an antioxidant, e.g., tocopherol, N-methyl-g-tocopheramine as well as butylated hydroxyanisole or butylated hydroxytoluene, can be admixed with the preparations.

The efficacy of the compounds in accordance with the invention in the treatment of photo-damaged skin will be evident from the experimental procedures described hereinafter:

Repair of UV-B-Caused Skin Damage in the Hairless Mouse

Hairless mice (HRS/J strain, Jackson Labs, aged 5–7 weeks at the beginning of the experiment) were irradiated three times a week with an arrangement of 8 Westinghouse irradiation lamps (FS40) which were placed about 20 cm above the animals. The radiation dose was controlled by a commercial phototherapeutic control device. The UV-B dose was chosen such that the dosage scarcely exceeded 0.06 J/cm$^2$, caused a minimal erythema, but no burning or scarring. After a total dose of about 3.5 J/cm$^2$ there resulted a significant elastosis which was evident from a histological report and which was confirmed by measuring the elastin using a radioimmunoassay for desmosin in the total skin. The desmosin content increased by two- to three-fold after 3.5 J/cm$^2$ UV-B irradiation. In order to make good the skin damage, the UV irradiation was interrupted and groups of animals were treated three times a week with different doses of compounds of formula I dissolved in acetone. These solutions were prepared freshly each week such that the dosage to be administered was present in 100 ml of acetone and were applied topically to an area of about 10 cm$^2$ on the backs of the animals. A controlled group was treated only with acetone.

After treatment for 10 weeks the animals were killed, skin preparations were prepared and the extent of the recovery was measured quantitatively by Luna staining of the elastin. In this experimental model the skin recovery is defined as the appearance of a normal dermis which extends from the epidermis to the layer of compressed elastin. The extent of the recovery was given by the width of this zone. The area of the zone on a standard length of the histological section was measured and the result was expressed as the total surface in mm$^2$ per 20 microscopic field. The results are compiled in Table I.

TABLE I

|  | Recovery Zone [mm$^2$ · 10$^{-3}$] |
|---|---|
| Control value | 1.2 ± 0.2 |
| Compound A, |  |
| 0.05 µg | 9.8 ± 2.8 |
| 2 µg | 27.2 ± 2.6 |
| 10 µg | 35.9 ± 7.5 |
| Control value | 1.67 ± 0.78 |
| Compound B, |  |
| 0.5 µg | 15.6 ± 2.74 |
| 2 µg | 20.5 ± 7.17 |
| Control value | 1.61 ± 0.68 |
| Compound C, |  |
| 2 µg | 32.8 ± 6.72 |
| 10 µg | 59.5 ± 6.71 |
| Control value | 3.3 ± 1.1 |
| Compound D, |  |
| 0.5 µg | 15.5 ± 4.9 |
| 2 µg | 19.1 ± 4.9 |

TABLE I-continued

|  | Recovery Zone [mm$^2$ · 10$^{-3}$] |
|---|---|
| 10 µg | 46.5 ± 6.9 |
| Compound E, |  |
| 0.5 µg | 7.48 ± 1.7 |
| 2 µg | 4.70 ± 2.0 |
| 10 µg | 22.2 ± 8.3 |

Compound A: p-[(E)-2-(3-Hexyl-5,6,7,8-tetrahydro-5,5,8,8-tetramethyl-2-naphthyl)vinyl]benzoic acid
Compound B: 4-[(E)-2-(3-Butyl-5,5,8,8-tetramethyl-5,6,7,8-tetrahydro-naphth-2-yl)vinyl]benzoic acid
Compound C: (all E)-7-(3-Hexyl-5,5,8,8-tetramethyl-5,6,7,8-tetrahydro-naphthalen-2-yl)-3-methyl-hepta-2,4,6-trienoic acid
Compound D: p-[(E)-2-(3-Ethyl-5,6,7,8-tetrahydro-5,5,8,8-tetramethyl-2-naphthyl)vinyl]benzoic acid
Compound E: p-[(E)-2-(3-Octyl-5,6,7,8-tetrahydro-5,5,8,8-tetramethyl-2-naphthyl)vinyl]benzoic acid.

The invention is illustrated further by the following Examples.

EXAMPLE 1

83 ml of hexylbenzene were treated with 1.8 g of aluminum chloride while cooling with ice. After brief stirring a solution of 40 g of 2,5-dichloro-2,5-dimethyl-hexane in 300 ml of carbon disulphide was added dropwise and the mixture was stirred at 0° C. for a further 2 hours. The reaction mixture was poured into ice/6N hydrochloric acid, extracted with ethyl acetate, dried over sodium sulphate and evaporated. The crude product was distilled in a high vacuum. There were obtained 25.5 g of 1,1,4,4-tetramethyl-6-hexyl-1,2,3,4-tetrahydro-naphthalene as a colourless oil, boiling point 141°–152° C./0.8 mm.

10 g of 1,1,4,4-tetramethyl-6-hexyl-1,2,3,4-tetrahydro-naphthalene were dissolved in 100 ml of carbon tetrachloride and, after the addition of a spatula tip of iron powder, treated dropwise at 0° C. with 6.4 g of bromine. After stirring at 0° C. for 3 hours the reaction mixture was poured into ice-water, extracted with ether and, after drying over sodium sulphate, evaporated. The crude product was purified by filtration over a silica gel column (eluent hexane/ethyl acetate=9:1) and gave 13 g of 1,1,4,4-tetramethyl-6-hexyl-7-bromo-1,2,3,4-tetrahydro-naphthalene as a pale yellow oil.

10 g of this bromide were dissolved in 100 ml of abs. tetrahydrofuran and treated dropwise at −78° C. with 40 ml of tert butyllithium, 1.4 molar in pentane. After stirring at −78° C. for 1 hour 60 ml of abs. dimethylformamide were added dropwise. The mixture was stirred at room temperature for a further 1 hour, then poured on to ice, acidified with 2N hydrochloric acid and extracted with ether. The organic phases were dried, evaporated and the crude product was filtered over a silica gel column (eluent hexane/ethyl acetate=19:1). 6.8 g of 2-formyl-3-hexyl-5,5,8,8-tetramethyl-5,6,7,8-tetrahydro-naphthalene were obtained as a yellowish oil.

3.2 g of sodium hydride, 50% in mineral oil, were washed twice with pentane and suspended in 50 ml of abs. dimethyl sulphoxide. After the dropwise addition of a solution of 20 g of diethyl (4-carbethoxybenzyl)phosphonate in 50 ml of dimethyl sulphoxide at about 15° C. the reaction mixture was stirred at room temperature for a further 2 hours. Thereafter, a solution of 9 g of 2-formyl-3-hexyl-5,5,8,8-tetramethyl-5,6,7,8-tetrahydro-naphthalene in 50 ml of abs. dimethyl sulphoxide was added dropwise and the mixture was heated to 40° C. for 3 hours. The reaction mixture was subsequently poured into ice-water acidified with 2N hydrochloric acid and extracted with ether. After drying the organic phase was evaporated and the crude product was filtered over a silica gel column. (eluent hexane/ethyl acetate=19:1). 5.0 g of ethyl p-[(E)-2-(3-hexyl-5,6,7,8-tetrahydro-5,5,8,8-tetramethyl-2-naphthyl)vinyl]benzoate were obtained as a yellowish oil.

8 g of this ester were dissolved in 50 ml of ethanol and treated with a solution of 10 g of potassium hydroxide in 10 ml of water and 20 ml of ethanol. After the addition of 50 ml of tetrahydrofuran the mixture was heated to 40° C. for 4 hours. The clear, yellow reaction solution was poured-into a mixture of ice and 6N hydrochloric acid, extracted with ethyl acetate, the organic phase was washed with water, dried and evaporated. After recrystallization of the crystalline residue from hexane/ethyl acetate there were obtained 6.2 g of p-[(E)-2-(3-hexyl-5,6,7,8-tetrahydro-5,5,8,8-tetramethyl-2-naphthyl)vinyl]benzoic acid in the form of white crystals, melting point 134°–136° C.

EXAMPLE 2

(E) -4- [2-(3 -Pentyl-5,5,8,8-tetramethyl-5,6,7,8-tetrahydro-naphthalen-2-yl)vinyl]benzoic acid was prepared in analogy to Example 1 starting from pentylbenzene. White crystals, melting point 173°–174° C. (from ethyl acetate).

EXAMPLE 3

(E)-4-[2-(3-Butyl-5,5,8,8-tetramethyl-5,6,7,8-tetrahydro-naphthalen-2-yl)vinyl]benzoic acid was prepared in analogy to Example 1 starting from butylbenzene. White crystals, melting point 192°–194° C. (from ethyl acetate/hexane).

EXAMPLE 4

4.1 g of sodium hydride, 50% in mineral oil, were washed with pentane and suspended in 70 ml of abs. dimethyl sulphoxide. After the dropwise addition of a solution of 24.5 g of ethyl (all-E)-6-(diethoxyphosphinyl)-3-methyl-2,4-hexadienoate in 70ml of abs. dimethyl sulphoxide at 15° C. the reaction mixture was stirred at room temperature for ½ hour, Thereafter; a solution of 11.3 g of 2-formyl-3-hexyl-5,5,8,8-tetramethyl-5,6,7,8-tetrahydro-naphthalene in 70 ml of dimethyl sulphoxide and 35 ml of tetrahydrofuran was added dropwise at 20° C. and the mixture was stirred at room temperature for a further 2 hours. The red-brown reaction mixture was subsequently poured into ice-water, acidified with 80 ml of 1N hydrochloric acid and extracted with ethyl acetate. The orange crude product was purified by flash chromatography (silica gel, eluent hexane/2% methyl tert.butyl ether). 8.5. g of ethyl (all-E)-7-(3-hexyl-5,5,8,8-tetramethyl-5,6,7,8-tetrahydro-naphthalen-2-yl)-3-methyl-hepta-2,4,6-trienoate were obtained as a pale yellowish oil. 4.1 g of methyl (2Z,4E,6E)-7-(3-hexyl-5,5,8,8-tetramethyl-5,6,7,8 -tetrahydro-naphthalen-2-yl)-3 -methyl -hepta-2,4,6-trienoate were isolated as the byproduct (non-polar compound) as a pale yellowish oil.

8.5 g of all-trans ester were dissolved in 160 ml of ethanol and 30 ml of tetrahydrofuran and treated with a solution of 12.8 g of potassium hydroxide in 60 ml of water. After stirring at 45° C. for 3 hours the majority of the ethanol was distilled off, the residue was poured on to ice and acidified with 1N hydrochloric acid. After extraction with ethyl acetate, drying and evaporation the crude product was recrystallized from ethyl acetate/hexane. 5.6 g of (all-E)-7-(3-hexyl-5,5,8,8-tetramethyl-5,6,7,8-tetrahydro-naphthalen-2-yl)-3-methyl-hepta-2,4,6-trienoic acid were obtained in the form of pale yellow crystals, melting point 173°–174° C.

EXAMPLE 5

(2E,4E,6E)-7-(3 -Pentyl-5,5,8,8-tetramethyl-5,6,7,8-tetrahydro-naphthalen-2-yl)-3-methyl-hepta-2,4,6-trienoic acid was prepared in analogy to Example 4 starting from 2-formyl-3-pentyl-5,5,8,8-tetramethyl-5,6,7,8-tetrahydro-naphthalene. Pale yellow crystals. Melting point 164°–166° C. (from ethyl acetate/hexane).

EXAMPLE 6

(2Z,4E,6E)-7 -(3 -Pentyl-5,5,8,8-tetramethyl-5,6,7,8-tetrahydro-naphthalen-2-yl)-3-methyl-hepta-2,4,6-trienoic acid was prepared by saponifying the corresponding ethyl ester from Example 4. Pale yellow crystals, melting point 170°–174° C. (from ethyl acetate/hexane).

EXAMPLE 7

1.4 g of sodium hydride, 50% in mineral oil, were suspended in 50 ml of abs. dimethyl sulphoxide and treated dropwise while cooling with ice with 8.5 g of 2-bromo-3-hydroxy-5,5,8,8-tetra-methyl-5,6,7,8-tetrahydro-naphthalene dissolved in 60 ml of abs. dimethylformamide. The reaction mixture was stirred at 40° C. for ½ hour and subsequently a solution of 4.4 g of propyl bromide in 20 ml of dimethylformamide was added while cooling with ice. After stirring at room temperature for 20 hours the mixture was poured into ice-water, extracted with ethyl acetate and the crude product obtained after drying and evaporation of the solvent was filtered over a silica gel column (eluent hexane/ethyl acetate=9:1). 9.5 g of 2-bromo-3-propoxy-5,5, 8,8-tetramethyl-5,6,7,8-tetrahydro-naphthalene were obtained as a brownish oil. This oil was dissolved in 100 ml of abs. tetrahydrofuran and treated dropwise at –78° C. with 40 ml of tert.butyllithium, 1.4 molar in pentane. After stirring at –78° C. for ½ hour 75 ml of abs. dimethylformamide were added dropwise and the mixture was stirred at room temperature for 1 hour. The pale beige suspension was poured into ice-water and extracted with ethyl acetate. After drying and evaporation of the organic phase the crude product was filtered over a silica gel column (eluent hexane/ 5% ether). There were obtained 6.6 g of 2-formyl-3-propoxy-5,5,8,8-tetramethyl-5,6,7,8-tetrahydro-naphthalene as a pale yellow oil which solidified upon cooling, melting point 51°–52° C.

1.3 g of sodium hydride, 50% in mineral oil, were suspended in 20 ml of abs. dimethyl sulphoxide (DMSO) and treated dropwise at 15° C. with a solution of 8.6 g of diethyl (4-carbethoxybenzyl)-phosphonate in 25 ml of abs. DMSO. The mixture was stirred at room temperature for 1 hour and then a solution of 3.3 g of the above aldehyde in 25 ml of abs. DMSO and 10 ml of tetrahydrofuran was added dropwise thereto. After stirring at 40° C. for 2 hours the mixture was poured into ice-water, acidified with 2N hydrochloric acid and extracted with ethyl acetate. After drying the organic phase with sodium sulphate and evaporation of the solvent the crude product was filtered over a silica gel column (eluent hexane/5% methyl tert.butyl ether). After recrystallization from hexane/ethyl acetate there were obtained 4.4 g of ethyl (E)-4-[2-(5,5,8,8-tetra-methyl-3-propoxy-5,6,7,8 -tetrahydro-naphthalen-2-yl)vinyl]benzoate in the form of white crystals, melting point 97°–100° C.

Saponification of this ester with a solution of 6.8 g of potassium hydroxide in 34 ml of water, 85 ml of ethanol and 20 ml of tetrahydrofuran at 45° C. for 4 hours gave, after acidification with 2N hydrochloric acid, extraction with ethyl acetate and recrystallization from ethyl acetate, 3.5 g of (E)-4-[2-(5,5,8,8-tetramethyl-3-propoxy-5,6,7,8-tetrahydro-naphthalen-2-yl)vinyl]benzoic acid in the form of white crystals, melting point 192° C.

EXAMPLE 8

(E)-4-[2-(5,5,8,8-Tetramethyl-3-pentoxy-5,6,7,8-tetrahydro-naphthalen-2-yl)vinyl]benzoic acid was prepared in analogy to Example 7 starting from 2-bromo-3-hydroxy-5,5,8,8-tetramethyl-5,6,7,8-tetrahydro-naphthalene and pentyl bromide. White crystals, melting point 148°–149° C. (from ethyl acetate).

EXAMPLE 9

In analogy to Example 4, from 8.4 g of ethyl (all-E)-6-dimethoxyphosphinyl-3-methyl-2,4-hexadienoate and 3.3 g of 2-formyl-3 -propoxy-5,5,8,8-tetramethyl-5,6,7,8-tetrahydro-naphthalene there were isolated 2.7 g of ethyl (2E,4E,6E)-3-methyl-7-(5,5,8,8-tetramethyl-3 -propoxy-5, 6,7,8-tetrahydro-naphthalen-2-yl)-hepta-2,4,6-trienoate, melting point 92°–93° C. (from hexane), and 1.5 g of the corresponding 2Z isomer as a yellow oil.

Saponification of the 2E isomer gave, after recrystallization from ethyl acetate, (2E,4E,6E)-3-methyl-7-(5,5,8,8-tetramethyl-3-propoxy-5,6,7,8-tetrahydro-naphthalen-2-yl)-hepta-2,4,6-trienoate in the form of yellow crystals, melting point 186° C.

Saponification of the 2Z isomer gave, after recrystallization from ethyl acetate, (2Z,4E,6E)-3-methyl-7-(5,5,8,8-tetramethyl-3-propoxy-5,6,7,8-tetrahydro-naphthalen-2-yl)-hepta-2,4,6-trienoic acid as yellow crystals of melting point 210°–211° C.

EXAMPLE 10

In analogy to Example 9, starting from 2-formyl-3-pentoxy-5,5,8,8-tetramethyl-5,6,7,8-tetrahydro-naphthalene there was obtained (2E,4E,6E)-3-methyl-7-(5,5,8,8-tetramethyl-3-pentoxy-5,6,7,8 -tetrahydro-naphthalen-2-yl)-hepta-2,4,6-trienoic acid, yellow crystals, melting point 162°–163° C. (from ethyl acetate) and, as a byproduct, (2Z,4E,6E)-3-methyl-7-(5,5,8,8-tetramethyl-3-pentoxy- 5,6, 7,8-tetrahydro-naphthalen-2-yl)-hepta-2,4,6-trienoic acid, yellow crystals, melting point 168°–169° C. (from ethyl acetate).

EXAMPLE 11

A spatula tip of Fe powder and then at 0° C. 680 ml of bromine dissolved in 20 ml of methylene chloride were added under argon to 3.76 g of 7,7-dimethyl-2-octyl-6,7,8, 9-tetrahydro-5H-benzo-cycloheptene in 30 ml of methylene chloride. After 5 hours the reaction mixture was poured on to ice, extracted with ethyl acetate, washed with sodium bisulphite solution, dried and evaporated. The crude product (4.43 g) contained 91% of 2-bromo-3-octyl-7,7-dimethyl-6, 7,8,9-tetrahydro-5H-benzocycloheptene in addition to 7% of regioisomers and was processed as follows in the crude state:

The crude product was dissolved in 25 ml of abs. tetrahydrofuran under argon and treated slowly at –78° C. with 7.51 ml of 1.55 M n-butyllithium. After 15 minutes at this temperature-2.37 ml of abs. dimethylformamide were added and the reaction mixture was warmed to room temperature. Thereafter, it was poured on to ice, extracted with diethyl ether, washed with sodium chloride solution, dried and evaporated. Flash chromatography on SiO$_2$ (hexane/ethyl acetate 97:3) gave 2.38 g of aldehyde as a colourless oil which was used as follows in, a Wittig reaction:

3.56 g of diethyl (4-carbethoxybenzyl)phosphonate were added at 0° C. under argon to 383 mg of sodium hydride (about 50% in oil) in 18 ml of abs. dimethylformamide. The reaction mixture was then stirred at room temperature for about 2 hours until the hydrogen evolution had finished. Thereafter, it was cooled to –10° C. and the aldehyde prepared above in 4 ml of abs. dimethyl-formamide was slowly added dropwise. Thereafter, the cooling bath was removed and the mixture was left to react at room temperature for 3 hours. The reaction mixture was poured on to ice, extracted with diethyl ether, washed with water, dried and evaporated. Flash chromatography on SiO$_2$ (hexane/ethyl acetate 98:2) gave 2.01 g of ethyl (E)-4-[2-(7,7-dimethyl-3-octyl-6,7,8,9-tetrahydro- 5H-benzocyclohepten-2-yl) vinyl]benzoate as a colourless oil which was hydrolyzed as follows:

The ester was dissolved in 20 ml of ethanol/tetrahydrofuran (1:1) and treated with 5.8 ml of 3N NaOH. Thereafter, the mixture was stirred at room temperature for 3 days, poured on to ice, acidified with 2N HCl, extracted with ethyl acetate, washed with water, dried and evaporated. Recrystallization from ethyl acetate yielded 1.56 g of (E)-4-[2-(7,7-dimethyl-3-octyl-6,7,8,9-tetrahydro-5H-benzoeyelohepten-2-yl)vinyl]benzoic acid as pale yellow crystals of melting point 179.5°–180.5° C.

EXAMPLE 12

Rac-(E) -4-[2-(5,7,7-trimethyl-3-octyl-6,7,8,9-tetrahydro-5H-benzocyclohepten-2-yl)vinyl]benzoic acid was obtained as pale yellow crystals of melting point 182°–183° C. in analogy to Example 11 from 7,7,9-trimethyl-2-octyl-6,7,8,9-tetrahydro-5H-benzocycloheptene The starting material was prepared from 7,7-dimethyl-3-octyl-6,7,8,9-tetrahydro-5H-benzocyclohepten-5-one by addition of methylmagnesium iodide in diethyl ether and subsequent de-oxygenation with trimethylsilyl chloride/sodium iodide/acetonitrile/hexane.

EXAMPLE 13

(E)-4-[2-(3-Butyl-5,5-dimethyl-6,7,8,9-tetrahydro-5H-benzocyclohepten-2-yl)vinyl]benzoic acid was obtained as white crystals of melting point 184°–186° C. in analogy to Example 11 from 2-butyl-9,9-dimethyl-6,7,8,9-tetrahydro-5H-benzocycloheptene.

The starting material was prepared as follows:

The corresponding Grignard compound was prepared under argon from 304 mg of Mg shavings and 2.50 g of 2-bromo- 9,9-dimethyl-6,7,8,9-tetrahydro-5H-benzocycloheptene in 25 ml of abs. tetrahydrofuran. After cooling to –15° C. 206 mg of CuI and 1.78 ml of 1-iodobutane were added in succession. The mixture was left to react at room temperature for 2 hours and then poured into ice/ammonium chloride solution. The solution was extracted with diethyl ether, washed with water, dried and evaporated. After filtration over SiO$_2$ with hexane as the eluent there were obtained 2.27 g of 2-butyl-9,9-dimethyl-6,7,8,9-tetrahydro-5H-benzo-cycloheptene (contaminated with 4% regioisomers and 6% 5,5-dimethyl-6,7,8,9-tetrahydro-5H-benzocyloheptene).

The following compounds were obtained analogously:

(E)-4- [2-(3-Hexyl-7,7 -dimethyl-indan-2-yl)vinyl] benzoic acid, white crystals of melting point 149°–150° C., (E)-4-[2-(3-hexyl-5,5 -dimethyl-6,7,8,9-tetrahydro-5H-benzocyclohepten-2-yl)vinyl]benzoic acid, colourless crystals of melting point 133°–134° C., and (E)-4-[2-(3-butyl-9,9-dimethyl-6,7,8,9-tetrahydro-5H-benzoeyclohepten-2-yl)vinyl]benzoic acid, white crystals of melting point 81°–83° C.

EXAMPLE 14

248 mg of NaH (about 50% in oil) were placed in 12 ml of abs. DMF under argon. 2.45 g of diethyl (4-carbethoxybenzyl)phosphonate were added thereto at 0° and the mixture was subsequently stirred at room temperature for about 2 hours until the $H_2$ evolution had finished. The mixture was cooled to –10° C. and 2.20 g of (5S,9SR,10RS)-10-t-butyldimethylsilyloxy-2-formyl-3-heptyloxy-5,9-dimethyl-6,7,8,9-tetrahydro-5,9-methano-5H-benzocycloheptene dissolved in 10 ml of abs. DMF were slowly added dropwise thereto. Then, the cooling bath was removed and the mixture was left to react at room temperature for 2 hours. It was then poured into ice/$NH_4Cl$ solution, extracted with diethyl ether, washed with NaCl solution, dried over $Na_2SO_4$ and concentrated. Flash chromatography on $SiO_2$ (hexane/ethyl acetate 98/2) gave 2.32 g of ethyl (E)-4-[2-[(5RS, 9S R, 10RS)-10-t-butyldimethylsilyloxy-3-heptyloxy-5,9-dimethyl-6,7,8,9-tetrahydro-5,9-methano-5H-benzocyclohepten-2-yl]vinyl]benzoate as a yellowish oil.

This oil was dissolved in 12 ml of abs. THF and treated with 3.72 g of tetrabutylammonium flouride. The mixture was stirred at 35° overnight and then poured on to ice. The mixture was extracted with diethyl ether, washed with water, dried over $Na_2SO_4$ and evaporated. Flash chromatography on $SiO_2$ (hexane/ethyl acetate 85/15) followed by crystallization from a small amount of hexane yielded 1.44 g of ethyl (E)-4-[2-[(5RS,9SR, 10RS)-3-heptyloxy-10-hydroxy-5,9-dimethyl-6,7,8,9-tetrahydro-5,9-methane-5H-benzocyclohepten-2-yl]vinyl]benzoate as yellowish crystals of melting point 78°–81° C.

1.255 g of (E)-4-[2-[(5RS,9SR,10RS)-3-heptyloxy-10-hydroxy-5,9-dimethyl-6,7,8,9-tetrahydro.-5,9-methano-5H-benzocyelohepten-2-yl]vinyl]benzoate were dissolved in 30 ml of ethanol/THF=1/1 and treated with 2.56 ml of 3N NaOH. The mixture was stirred at room temperature for 5 hours, then poured into ice/conc. HCl, extracted with ethyl acetate, washed with water, dried over $Na_2SO_4$ and evaporated. Recrystallization from hexane/ethyl acetate yielded 873 mg of (E)-4-[2-[(5RS,9SR,10RS)-3-heptyloxy-10-hydroxy-5,9-dimethyl-6,7,8,9-tetrahydro-5,9-methano-5H-benzocyclohepten-2-yl]vinyl]benzoic acid as yellow crystals of melting point 89°–90° C.

The starting, material was prepared as follows:

4-Bromoheptyloxybenzene and 2,6-dimethylcyelohexanone were convened with $NaNH_2$ into (5RS,9SR,10RS)-2-heptyloxy-10-hydroxy-5,9-dimethyl-6,7,8,9-tetrahydro-5,9-methano-5H-benzocycloheptene which was brominated with $Br_2$ and iron as the catalyst.

4.49 g of the thus-obtained (5RS,9SR,10RS)-2-bromo-3-heptyloxy-10-hydroxy-5,9-dimethyl-6,7,8,9-tetrahydro-5,9-methano-5H-benzocycloheptene were placed in 12 ml of $CH_2Cl_2$ under argon and treated with 2.58 ml of 2,6-llutidine followed by 3.08 ml of t-butyldimethylsilyl triflate. The mixture was stirred at 35° C. overnight and then poured on to ice. The mixture was extracted with diethyl ether, washed with 1N HCl and water, dried over $Na_2SO_4$ and evaporated. Column filtration ($SiO_2$/hexane) gave 5.39 g of (5RS,9SR,10RS)-2-bromo-10-t-butyldimethylsilyloxy-3-heptyloxy-5,9-dimethyl-6,7,8,9-tetrahydro-5,9 -methano-5H-benzocyeloheptene as a colourless oil.

4.85 g thereof were placed in 25 ml of abs. THF under argon and treated at –78° C. with 7.0 ml of 1.5M nBuLi (hexane). The reaction mixture was held at this temperature for ¼ hour, then 2.20 ml of abs. DMF were added dropwise thereto in undiluted form and the cooling bath was subsequently removed. After ½ hour at room temperature the mixture was poured on to ice, extracted with diethyl ether, washed with water, dried over $Na_2SO_4$ and evaporated. Flash chromatography on $SiO_2$ (hexane/ethyl acetate 88/2) gave 4.01 g of (5RS,9SR,10RS)-10-t-butyldimethylsilyloxy-2-formyl-3-heptyloxy-5,9-dimethyl-6,7,8,9-tetrahydro-5,9-methano-5H-benzocycloheptene as colourless crystals of melting point 66.67° C.

EXAMPLE 15

In analogy to Example 14 there were prepared ethyl (E)-4-[2-[(5RS,9SR,10RS)-3-butoxy-10-hydroxy-5,9-dimethyl-6,7,8,9-tetrahydro-5,9-methano-5H-benzocyclohepten-2-yl]vinyl]benzoate as colourless crystals of melting point 104°–106° C. and therefrom (E)-4-[2-[(5RS, 9SR, 10RS)-3-butoxy-10-hydroxy-5,9-dimethyl-6,7,8,9-tetrahydro-5,9-methano-5H-benzocyclohepten-2-yl]vinyl] benzoic acid as white crystals of melting point 129°–130° C.

EXAMPLE 16

4.6g of ethyl p-[(E)-2-(3-hexyl-5,6,7,8-tetrahydro-5,5,8,8-tetramethyl-2-naphthyl)vinyl]benzoate were dissolved in 140 ml of carbon tetrachloride and, after the addition of 2 g of N-bromosuccinimide and a spatula tip of a,a'-azoisobutyronitrile, heated at reflux for 1 hour. After cooling the separated succinimide was filtered off, the organic phase was concentrated and the oily residue was filtered over neutral Alex. 5.6 g of a yellow, viscous oil were obtained.

This oil (5.6 g) was dissolved in 125 ml of acetic acid and treated with 2.5 g of silver acetate. After stirring at room temperature for 7 hours the suspension was filtered over Dicalite, washed several times with tert.butyl methyl ether, the filtrate was treated with ice-water and extracted with tert.butyl methyl ether. After washing the organic phase with water, sodium bicarbonate solution; and sodium chloride solution it was dried over sodium sulphate and evaporated. There-were obtained 5.5 g of a yellow oil which was purified further by chromatography (silica gel, eluent hexane/5% ethyl acetate) and which gave 3.8 g of ethyl (E)-(RS)-4-[2-[3-(1-acetoxy-hexyl)-5,5,8,8-tetramethyl-5,6,7,8-tetrahydro-naphthalen-2-yl]vinyl]benzoate as a pale yellow, viscous oil. 1.4 g of this ethoxy compound were dissolved in 36 ml of tetrahydrofuran and, after the addition of 36 ml of methanol, treated with 280 mg of finely powdered potassium carbonate. After stirring at room temperature for 8 hours the mixture was evaporated at 30° C. and the crude product was purified by chromatography (silica gel, eluent hexane/tert.butyl methyl ether=8:2). 1.1 g of a pale yellow oil were obtained. (Compound XI: $R^1$=(b); $R^{10}$=ethoxycarbonyl; $R^{12}$=n-pentyl; $R^8$+$R^9$=ethylene; $R^4$–$R^7$=methyl).

1.5 g of this oil were dissolved in 40 ml of methylene chloride and treated with 3 g of manganese dioxide. After stirring at room temperature for 8 hours 3 g of manganese dioxide were again added and the mixture was stirred for a further 22 hours. After filtration over Dicalite the filtrate was evaporated and the oily residue was filtered over silica gel (eluent hexane/tert.butyl methyl ether=9:1). There were obtained 1.4 g of a yellow oil which was dissolved in a mixture of 50 ml of ethanol and 25 ml of tetrahydrofuran and treated with a solution of 2.3 g of potassium hydroxide in 20 ml of water and 20 ml of ethanol. After stirring at room temperature for 4 hours the mixture was acidified with 2N hydrochloric acid and extracted several times with ethyl acetate. After washing, drying and evaporation there were obtained 1.4 g of a crystalline material which was recrystallized from hexane/ethyl acetate and gave 1.1 g of (E)-4-[2-(3-hexanoyl-5,5,8,8-tetramethyl-5,6,7,8-tetrahydro-naphthalen-2-yl)vinyl]benzoic acid in the form of colourless crystals, melting point 118°–119° C.

EXAMPLE 17

10 g of 1,1,4,4-tetramethyl-6-pentyl-7-bromo-1,2,3,4-tetrahydro-naphthalene were dissolved in 47 ml of piperidine and treated under argon in succession with 450 mg of tetrakis(tri-phenylphosphine)palladium, 88 mg of copper(I) iodide and 130 mg of triphenylphospine. A solution of 8.6 ml of ethynyl-trimethylsilane in 47 ml of pyridine was-added dropwise in the course of 3.5 hours at an internal temperature of 95° C. After stirring at 95° C. for 4 hours a further 1.5 ml of ethynyl-trimethylsilane were slowly added dropwise and the reaction mixture was stirred at 95° C. for a further 15 hours. After cooling the mixture was poured on to ice, acidified with 37% hydrochloric acid and extracted with hexane. After washing, drying and evaporation there was obtained a red oil which gave 7.9 g of a pale yellow oil after filtration over silica gel (eluent hexane).

8.1 g of this oil were dissolved in 80 ml of tetrahydrofuran and treated with 8 g of tetrabutylammonium fluoride. After stirring at room temperature for ½ hour the mixture was poured into ice-water and extracted with hexane. The red-brown oil obtained after drying and evaporation was filtered over silica gel (eluent hexane) and gave 5.8 g of a pale beige oil.

This oil (5.8 g) was dissolved in 25 ml of tetrahydrofuran and treated dropwise with 15.5 ml of n-butyllithium (1.6 molar in hexane) while cooling with dry ice. After stirring at –78° C. for 1 hour 15.5 ml of dimethylformamide were added dropwise and the mixture was stirred at room temperature for 1 hour. The reaction mixture was subsequently poured into ice-water, acidified with 3N hydrochloric acid and extracted with ethyl acetate. The orange oil obtained after drying and evaporation was filtered over silica gel (eluent hexane/ethyl acetate=8:2) and gave 5.8 g of a yellow oil which crystallized in the cold. (Compound II: A=formyl, $R^2$=n-pentyl, $R^8$+$R^9$=ethylene, $R^4$–$R^7$=methyl.)

2 g of sodium hydride (50% in mineral oil) were washed twice with pentane, suspended in 38 ml of dimethylsulphoxide and treated dropwise at 15° C. with a solution of 11.3 g of ethyl 4-diethoxyphosphinyl-3-methyl-crotonate in 38ml of dimethyl sulphoxide. After stirring at room temperature for 1 hour a solution of 5.8 g of the substituted propargyl aldehyde (as described above) in 40 ml of tetrahydrofuran was added dropwise. The reaction mixture was stirred at room temperature for 2 hours, subsequently poured into ice-water, acidified with 2N hydrochloric acid and extracted with ethyl acetate. The dark red oil obtained after drying and evaporation was firstly filtered over silica gel (eluent hexane/5% tert.butyl methyl ether) and subsequently .separated using medium pressure chromatography (eluent hexane/2% tert.butyl methyl ether). There were obtained 1.8 g of ethyl (2E,4E)-3-methyl-7-(5,5,8,8-tetramethyl-3-pentyl-5,6,7,8 -tetrahydronaphthalen-2-yl)-hepta-2,4-dien-6-ynoate and 1.2 g of the corresponding (2Z,4E) compound as yellowish oils.

1.8 g of the (2E,4E) compound were dissolved in 36 ml of ethanol and 15 ml of tetrahydrofuran and treated with a solution of 2.8 g of potassium hydroxide in 13 ml of water. After stirring at 50° C. for 2 hours the reaction mixture was evaporated to half, poured into ice-water, acidified with 1N hydrochloric acid and extracted with ethyl acetate. The crystalline product obtained after drying and evaporation was recrystallized from hexane and gave 1.2 g of (2E,4E)-3-methyl-7-(5,5,8,8-tetramethyl-3-pentyl-5,6,7,8-tetrahydro-naphthalen-2-yl)-hepta-2,4-dien-6-ynoic acid in the form of white crystals, melting point 155°–156° C.

In analogy thereto, saponification of the (2Z,4E) ester gave 0.9 g of the (2Z,4E) acid, melting point 165°–166° C.

EXAMPLE 18

(2E,4E)-3 -Methyl-7-(5,5,8,8-tetramethyl-3 -hexyl-5,6,7,8-tetrahydro-naphthalen-2-yl)-hepta-2,4-dien-6-ynoic acid was obtained in analogy to Example 17 starting from 1,1,4,4-tetramethyl-6-hexyl-7-bromo-1,2,3,4-tetrahydronaphthalene.

EXAMPLE 19

190 mg of NaH (50% in mineral oil) were placed in 8 ml of abs. DMF under argon and 1.43 g of diethyl (2E,4E)-6-(diethoxy-phosphinyl)-3-methyl-2,4-hexadienoate were added thereto at 0°. After completion of the $H_2$ evolution the mixture was left to stir at room temperature for a further 30 min., before 1.37 g of (5RS,9SR,10RS)-2-bromo-3-butoxy-10-t-butyldimethylsilyloxy-5,9-dimethyl-6,7,8,9-tetrahydro-5,9-methane-5H-benzocycloheptene dissolved in 4 ml of abs. DMF were added dropwise at 0°. After 1 h. at room temperature the mixture was poured on to ice, extracted with diethyl ether, washed with saturated NaCl soln. and water, dried over $Na_2SO_4$ and evaporated under reduced pressure. Medium pressure chromatography on $SiO_2$ (hexane/ethyl acetate=98.5/1.5) gave, in addition-to non-polar fractions in which the 2Z isomer was enriched, 1.33 g of ethyl (2E,4E,6E)-(5RS,9SR,10RS)-7-(3-butoxy-10-t-butyldimethylsilyloxy-5,9-dimethyl-6,7,8,9-tetrahydro-5,9-methano-5H -benzocyclohepten-2-yl)-3-methyl-hepta-2,4,6-trienoate as a yellow foam which was slightly contaminated with other isomers.

1.33 g of the foregoing compound were dissolved in 14 ml of abs. THF and treated under argon overnight at 35° with 3.0 g of $nBu_4NF$. The mixture was poured on to ice, extracted with diethyl ether, washed with water, dried and evaporated. Flash chromatography and subsequent medium pressure chromatography on $SiO_2$ (hexane/ethyl acetate=9/1) yielded 370 mg of ethyl (2E,4E,6E)-(5RS,9SR,10RS)-7-(3-butoxy-10-hydroxy-5,9-dimethyl-6,7,8,9-tetrahydro-5,9-methano-5H-benzocyclohepten-2-yl)-3-methyl-hepta-2,4,6-trienoate as a yellow foam.

This ester was dissolved in 7 ml of ethanol/THF=1/1 and treated under argon with 2.1 ml of 2N NaOH. The mixture was left to react at room temperature for 64 h. and then poured into ice/HCl/ethyl acetate. The organic phase was washed twice with water, dried and evaporated. Recrystallization from hexane/ethyl acetate=7/3 yielded 153 mg of (2E,4E,6E)-(5RS,9SR,10RS)-7-(3-butoxy-10-hydroxy-5,9-dimethyl-6,7,8,9-tetrahydro-5,9-methano-5H-benzocyclohepten-2-yl)-3-methyl-hepta-2,4,6-trienoic acid as yellow crystals of m.p. 176°–178°.

The (5RS,9SR,10RS)-2-bromo-3-butoxy-10-t-butyldimethylsilyloxy-5,9-dimethyl-6,7,8,9-tetrahydro-5,9-methano-5H-benzocycloheptene required as the starting material was prepared in analogy to the procedure described in Example 14 from the building blocks p-bromophenol, 1-iodobutane and 2,6-dimethylcyclohexanone.

EXAMPLE 20

1.02 g of NaH (50% in mineral oil) were placed in 60 ml of abs. DMF under argon and 6.0 g of 3-bromo-5,5,8,8- tetramethyl-5,6,7,8-tetrahydro-2-naphthol were added thereto at 0°. The mixture was left to stir at 0° for 1 h. and then 2.28 ml of propargyl bromide were added dropwise thereto. The cooling bath was removed and the mixture was left to react for 2 h. The mixture was poured on to ice, extracted with diethyl ether, the organic phase was washed with water and saturated NaCl soln., dried and the solvent was removed under reduced pressure. Flash chromatography on $SiO_2$ (hexane/ethyl acetate=99/1) gave 6.62 g of 2-bromo-3-propargyloxy-5,5,8,8-tetramethyl-5,6,7,8-tetrahydro-2-naphthalene as white crystals of m.p. 65°–66°.

24 mmol of a lithium diisopropylamide solution (about 0.25 M) were prepared according to standard procedures and then 6.62 g of 2-bromo-3-propargyloxy-5,5,8,8-tetramethyl-5,6,7,8 -tetrahydro -2-naphthalene dissolved in 15 ml of THF were added dropwise thereto at 0°. After 30 min., always at 0°, 2.53 ml of ethyl iodide and 2.5 ml of DMPU (1,3-dimethyl-3,4,5,6-tetrahydro-2-(1H)-pyrimidinone) were added. After 4 h. the mixture was poured on to ice, extracted with diethyl ether, washed with water and saturated NaCl soln., dried and evaporated under reduced pressure. Flash chromatography on $SiO_2$ (hexane/ethyl acetate=98.5/1.5) yielded 4.35 g of ethylated product.

This product was placed in 50 ml of abs. THF under argon and subjected to a metal/halogen exchange by treatment with 9.25 ml of 1.6 M nBuLi (hexane). After 15-min. 2.8 ml of abs. DMF were sprayed into the mixture-and the cooling bath was subsequently removed. After 1 h. the reaction mixture was poured on to ice, the product was extracted with diethyl ether, washed with water and saturated NaCl solution, dried and evaporated under reduced pressure. Flash chromatography on $SiO_2$ (hexane/ethyl acetate=96/4) gave 2.17 g of 2-formyl-3-pent-2-ynyloxy-5,5,8,8-tetramethyl-5,6,7,8-tetrahydro-naphthalene as yellowish crystals of m.p. 90°–91°.

193 mg of NaH (55% in mineral oil) were placed in 10 ml of abs. DMF under argon and 1.66 g of diethyl (4-carbethoxybenzyl)-phosphonate were added thereto at 0° and the mixture was subsequently stirred at room temperature until the $H_2$ evolution had finished. Then, 1.08 g of 2-formyl-3-pent-2-ynyloxy-5,5,8,8-tetramethyl-5,6,7,8-tetrahydro-naphthalene without addition solvent were added at 0°. After 30 min. at room temperature the mixture was extracted with hexane and washed twice with ethanol/$H_2O$= 8/2. Drying, evaporation and direct crystallization from hexane yielded 1.45 g of ethyl (E)-4-[2-(3-pent-2-ynyloxy-5,5,8,8-tetramethyl-5,6,7,8-tetrahydro-naphthalen-2-yl)-vinyl]-benzoate as yellowish crystals of m.p. 80°–82°.

1.30 g of ethyl (E)-4-[2-(3-pent-2-ynyloxy-5,5,8,8-tetramethyl-5,6,7,8-tetrahydro-naphthalen-2-yl)-vinyl]-benzoate were placed in 10 ml of abs. ethanol/THF=1/1 and treated under argon with 4.9 ml of 3 N NaOH. After 40 h. at room temperature the mixture was poured on to ice and extracted with ethyl acetate. The organic phase was washed with water and saturated NaCl soln., dried and evaporated. Crystallization from hexane/ethyl acetate yielded 1.07 g of (E)-4-[2-(3-pent-2-ynyloxy-5,5,8,8-tetramethyl-5,6,7,8-tetrahydro-naphthalen-2-yl)-vinyl]-benzoic acid as beige crystals of m.p. 144°–145°.

EXAMPLE 21

212 mg of NaH (50% in mineral oil) were placed in 8 ml of abs. DMF under argon and 1.50 g of undiluted diethyl (2E,4E)-6-(diethoxyphosphinyl)-3-methyl-2,4-hexadienoate were added dropwise at 0°. After completion of the $H_2$ evolution 1.10 g of 2-formyl-3 -pent-2-ynyloxy-5,5,8,8-tetramethyl-5,6,7,8-tetrahydro-naphthalene (see Ex. 20) were added thereto and the mixture was left to react at room temperature for 1.5 h. The reaction mixture was poured on to ice, extracted with hexane, washed twice with ethanol/$H_2O$=8:2, dried and evaporated. Flash chromatography on $SiO_2$ (hexane/ethyl acetate=98.5/1.5) yielded, in addition to 412 mg of 2Z isomers in the non-polar fractions, 1026 mg of ethyl (2E,4E,6E)-3-methyl-7-(3-pent-2-ynyloxy-5,5,8,8-tetramethyl-5,6,7,8-tetrahydro-naphthalen-2-yl)-hepta-2,4,6-trienoate as a yellow oil.

1.02 g of ethyl (2E,4E,6E)3-methyl-7-(3-pent-2-ynyloxy-5,5,8,8-tetramethyl-5,6,7,8-tetrahydro-naphthalen-2-yl)-hepta-2,4,6-trienoate were placed in 8 ml of abs. THF/ethanol (1/1) and treated under argon with 3.9 ml of 3N NaOH. The mixture was stirred at room temperature for 2 days and at 400 for 3 h. Then, the mixture was poured on to ice/HCl, extracted with diethyl ether, washed with water, dried and evaporated. Crystallization from diethyl ether yielded 644 mg of (2E,4E,6E)-3-methyl-7-(3-pent-2-ynyloxy-5,5,8,8-tetramethyl-5,6,7,8-tetrahydro-naphthalen-2-yl)-hepta-2,4,6-trienoic acid as yellow crystals of m.p. 208°–209°.

EXAMPLE 22

In analogy to Example 20 using allyl bromide as the electrophile in the first step there is prepared (E)-4- [2-(3 -allyloxy-5,5,8,8 -tetramethyl-5,6,7,8-tetrahydro-naphthalen-2-yl)-vinyl]-benzoic acid of m.p. 191°–192°;

and using crotyl bromide as the electrophile in the first step there is prepared 4-[(E)-2-((E)-3-but-2-enyloxy-5,5,8,8-tetramethyl-5,6,7, 8-tetrahydro-naphthalen-2-yl)-vinyl]-benzoic acid of m.p. 178°–180°.

EXAMPLE 23

In analogy to Example 21, using allyl bromide as the electrophile in the first step (see also Ex. 20) there is prepared (2E,4E,6E)-7 -(3 -allyloxy-5,5,8,8-tetramethyl-5,6,7,8-tetrahydro-naphthalen-2-yl)-3-methyl-hepta-2,4,6-trienoic acid of m.p. 193°–194°;

and using crotyl bromide as the electrophile in the first step there is prepared (2E,4E,6E)-7-[(E)-3-but-2-enyloxy-5,5,8,8-tetramethyl-5,6,7,8 -tetrahydro-naphthalen-2-yl)-3 -methyl-hepta-2,4,6-trienoic acid 196°–198°.

Example A

Hard gelatine capsules can be produced as follows:

| Ingredients | mg/capsule |
| --- | --- |
| 1. Spray-dried powder containing 75% compound I | 20 |
| 2. Sodium dioctylsulphosuccinate | 0.2 |
| 3. Sodium carboxymethylcellulose | 4.8 |
| 4. Microcrystalline cellulose | 86.0 |
| 5. Talc | 8.0 |
| 6. Magnesium stearate | 1.0 |
| Total | 120 |

The spray-dried powder, which is based on the active ingredient, gelatine and microcrystalline cellulose and which has an average active ingredient particle size of <1 m (measured by autocorrelation spectroscopy), is moistened with an aqueous solution of sodium carboxymethylcellulose and sodium dioctylsulphosuccinate and kneaded. The resulting mass is granulated, dried and sieved, and the granulate obtained is mixed with microcrystalline cellulose, talc and magnesium stearate. The mixture is filled into size 0 capsules.

Example B

Tablets can be produced as follows:

| Ingredients | mg/tablet |
| --- | --- |
| 1. Compound I as a finely milled powder | 20 |
| 2. Powd. lactose | 100 |
| 3. White corn starch | 60 |
| 4. Povidone K30 | 8 |
| 5. White corn starch | 112 |
| 6. Talc | 16 |
| 7. Magnesium stearate | 4 |
| Total | 320 |

The finely milled substance is mixed with lactose and a portion of the corn starch. The mixture is moistened with an aqueous solution of Povidone K30 and kneaded, and the resulting mass is granulated, dried and sieved. The granulate is mixed with the remaining corn starch, talc and magnesium stearate and pressed to tablets of suitable size.

Example C

Soft gelatine capsules can be produced as follows:

| Ingredients | mg/capsule |
| --- | --- |
| 1. Compound I | 5 |
| 2. Triglyceride | 450 |
| Total | 455 |

10 g of compound I are dissolved in 90 g of medium chain triglyceride with stirring, inert gasification and protection from light. This solution is processed as a capsule fill mass to soft gelatine capsules containing 5 mg of active ingredient.

Example D

A lotion can be prepared as follows:

| Ingredients | |
| --- | --- |
| 1. Compound I, finely milled | 1.0 g |
| 2. Carbopol 934 | 0.6 g |
| 3. Sodium hydroxide | q.s. ad pH 6 |
| 4. Ethanol, 94% | 50.0 g |
| 5. Demineralized water | ad 100.0 g |

The active ingredient is incorporated into the 94% ethanol/water mixture with protection from light. Carbopol 934 is stirred in until gelling is complete and the pH value is adjusted with sodium hydroxide.

Example E

A cream can be produced from the ingredients listed hereinafter in a manner known per se:

| | Wt. % |
| --- | --- |
| Compound of formula I | 0.1–5 |
| Cetyl alcohol | 5.25–8.75 |
| Arlacel 165 (glyceryl/PEG 100 stearate) | 3.75–6.25 |
| Miglyol 818 (caprylic/capric/linoleic acid) | 11.25–18.75 |
| Sorbitol solution | 3.75–6.25 |
| EDTA Na$_2$ | 0.075–0.125 |
| Carbopol 934P (carbomer 934P) | 0.15–0.25 |
| Butylated hydroxyanisole | 0.0375–0.0625 |
| Methylparaben | 0.135–0.225 |
| Propylparaben | 0.0375–0.0625 |
| NaOH (10% solution) | 0.15–0.25 |
| Water q.s. | 100.00 |

Example F

A gel can be produced from the ingredients listed hereinafter in a manner known per se:

| | Wt. % |
| --- | --- |
| Compound of formula I | 0.1–5 |
| Pluronic L 101 (poloxamer 331) | 10.00 |
| Aerosil 200 (silicion dioxide) | 8.00 |
| PCL liquid (fatty acid ester | 15.00 |
| Cetiol V (decyl oleate) | 20.00 |
| Neobee oil (medium chain length triglyceride) | 15.00 |
| Euhanol G (octyldodecanol), q.s. | 100.00 |

The physical properties of the preparations can be altered by varying the ratio between the adjuvants of Examples E and F.

We claim:

1. A method of treating photodamaged skin comprising topically administering to said photodamaged skin a composition which comprises a compound of the formula:

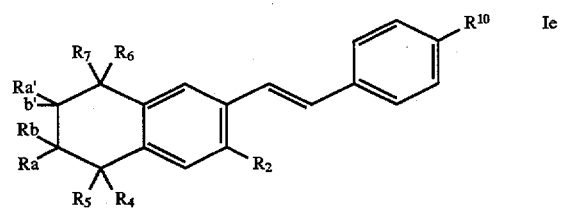

wherein $R^2$ is $C_{2-8}$-alkanoyl, $C_{2-8}$-alkyl, $C_{2-8}$-alkenyl, $C_{2-8}$-alkynyl or —OCH$_2$R$^3$;

$R^3$ is hydrogen, $C_{1-6}$-alkyl, $C_{2-6}$-alkenyl or $C_{2-6}$-alkynyl;

$R^5$ and $R^7$ each independently are hydrogen or $C_{1-5}$-alkyl;

$R^4$ and $R^6$ each independently are hydrogen or $C_{1-5}$-alkyl, or taken together are methylene or ethylene which are unsubstituted or substituted by hydroxy;

$R^a$, $R^{a'}$, $R^b$ and $R^{b'}$ each are independently hydrogen or $C_{1-5}$-alkyl;

$R^{10}$ is carboxyl, $C_{1-6}$-alkoxycarbonyl or mono- or di-($C_{1-6}$-alkyl)carbamoyl;

and pharmaceutically acceptable salts of carboxylic acids of formula Ie;

and a pharmaceutically acceptable carrier, wherein said composition is administered in an amount sufficient to treat said photodamaged skin.

2. The method of claim 1 wherein $R^2$ is $C_{2-8}$ alkyl.

3. The method of claim 2 wherein $R^a$, $R^{a'}$, $R^b$ and $R^{b'}$ are hydrogen.

4. The method of claim 3 wherein $R^4$, $R^5$, $R^6$, and $R^7$ are independently hydrogen or methyl, or $R^5$ and $R^7$ are independently hydrogen or methyl and $R^4$ and $R^6$ taken together are methylene or ethylene which are unsubstituted or substituted by hydroxy.

5. The method of claim 4 wherein $R^4$, $R^5$, $R^6$, and $R^7$ are all methyl.

6. The method of claim 5 wherein said compound is p-[(E)-2-(3-hexyl-5,6,7,8-tetrahydro-5,5,8,8-tetramethyl-2-naphthyl)vinyl]benzoic acid.

7. The method of claim 6 wherein said compound is present in said composition in an amount from about 0.1% to about 5% by weight of the composition.

8. The method of claim 7 wherein said compound is present in said composition in an amount from about 0.3% to about 2% by weight of the composition.

9. The method of claim 5 whereto said compound is (E)-4-[2-(3-Pentyl-5,5,8,8-tetramethyl-5,6,7,8-tetrahydronaphthalen-2-yl)vinyl]benzoic acid.

10. The method of claim 9 wherein said compound is present in said composition in an amount from about 0.1% to about 5% by weight of the composition.

11. The method of claim 10 wherein said compound is present in said composition in an amount from about 0.3% to about 2% by weight of the composition.

12. The method of claim 5 wherein said compound is (E)-4-[2-(3-Butyl-5,5,8,8-tetramethyl-5,6,7,8-tetrahydronaphthalen-2-yl)vinyl]benzoic acid.

13. The method of claim 12 wherein said compound is present in said composition in an amount from about 0.1% to about 5% by weight of the composition.

14. The method of claim 13 wherein said compound is present in said composition in an amount from about 0.3% to about 2% by weight of the composition.

\* \* \* \* \*